US006653256B1

(12) United States Patent
Wolf et al.

(10) Patent No.: US 6,653,256 B1
(45) Date of Patent: *Nov. 25, 2003

(54) MICROCAPSULE FORMULATIONS

(75) Inventors: Hilmar Wolf, Langenfeld (DE); Joachim Weissmüller, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/786,259

(22) PCT Filed: Aug. 24, 1999

(86) PCT No.: PCT/EP99/06199

§ 371 (c)(1), (2), (4) Date: Mar. 1, 2001

(87) PCT Pub. No.: WO00/13504

PCT Pub. Date: Mar. 16, 2000

(51) Int. Cl.$^7$ ............... A01N 57/00; A01N 43/40; A01N 43/72; A01N 43/66; A01N 43/60
(52) U.S. Cl. ............ 504/127; 504/128; 504/130; 504/195; 504/196; 504/223; 504/227; 504/235; 504/244
(58) Field of Search ................. 504/359, 127, 504/128, 130, 195, 196, 223, 227, 235, 244

(56) References Cited

U.S. PATENT DOCUMENTS

| | | | |
|---|---|---|---|
| 4,181,639 A | 1/1980 | Bomer et al. | 260/29.6 WB |
| 4,253,682 A | 3/1981 | Baatz et al. | 282/27.5 |
| 5,342,556 A | 8/1994 | Träubel et al. | 264/4.7 |
| 5,925,595 A | 7/1999 | Seitz et al. | 504/116 |
| 6,020,066 A | 2/2000 | Weisser et al. | 428/402.21 |

FOREIGN PATENT DOCUMENTS

| | | |
|---|---|---|
| DE | 1248016 | 8/1967 |
| DE | 3016189 | 10/1981 |
| EP | 0 322 820 | 7/1989 |
| EP | 0 841 088 | 5/1998 |
| GB | 2206492 | * 1/1989 |
| WO | 00/13504 | 3/2000 |

* cited by examiner

Primary Examiner—Alton Pryor
(74) Attorney, Agent, or Firm—Richard E. L. Henderson; Raymond J. Harmuth

(57) ABSTRACT

Microcapsule formulations of

A) a particulate disperse phase of
  a) a reaction product of
    at least one diamine, polyamide, dialcohol, polyalcohol and/or aminoalcohol with
    an isocyanate mixture characterized in the description, if appropriate as a mixture with toluylene diisocyanate,
  b) at least one agrochemically active compound of a particular group of substances and,
  c) if appropriate, additives, and B) a liquid aqueous phase, a process for the preparation of these formulations, and their use for applying the active compounds which they comprise.

9 Claims, No Drawings

MICROCAPSULE FORMULATIONS

This appln. is a 3H of PCT/EP99/06199 filed Aug. 24, 1999.

The present invention relates to new microcapsule formulations of agrochemically active compounds, to a process for their preparation, and to their use for applying agrochemically active compounds.

It is already known to stir agrochemically active compounds in the form of emulsifiable concentrates or wettable powders with water and to spray the plants with the resulting ready-to-use spray mixtures. The disadvantage of this method is that it is frequently very complicated to guarantee sufficient protection for the persons who apply these spray mixtures.

Furthermore, it has already been described that agrochemically active compounds can be applied in the form of aqueous microcapsule suspensions (cf. DE-A 3 016 189, DE-B 1 185 15, DE-B 1 248 016 and DE-A 2 734 577). However, it is inconvenient that such preparations often tend to agglomerate and that the active components which they contain are not always liberated in the desired quantity and over the intended prolonged period.

Finally, it can be seen from WO 98-29 360 that plant nutrients can be microencapsulated with the aid of isocyanate mixtures and polyols. However, the use of such isocyanate mixtures for microencapsulating agrochemically active compounds has not been disclosed as yet.

There have now been found new microcapsule formulations which are composed of
A) a particulate disperse phase of
  a) a reaction product of
    at least one diamine, polyamine, dialcohol, polyalcohol and/or aminoalcohol with
    an isocyanate mixture obtained during the dimerization and/or trimerization of hexamehtylene-1,6-diisocyanate, of the formula

    OCH—(CH$_2$)$_6$—NCO      (I)

and/or during the reaction of hexamethylene-1,6-diisocyanate, of the formula (I), with water and/or carbon dioxide,
    if appropriate in a mixture with toluylene diisocyanate,
  b) at least one fungicidally active compound from the group of the amino derivatives, the morpholine derivatives or the azole derivatives and/or
    at least one insecticidally active compound from the group of the phosphoric esters, the pyrethroids or the carbamates and/or
    at least one herbicidal active compound from the group of the acetanilides and
  c) if appropriate, additives, the particles of the disperse phase having a mean particle size of between 1 and 20 μm and
B) a liquid aqueous phase.

Furthermore, it has been found that the microcapsule formulations according to the invention can be prepared by, mixing at least one fungicidally active compound from the group of the amino derivatives, the morpholine derivatives or the azole derivatives and/or
  at least one insecticidally active compound from the group of the phosphoric esters, the pyrethroids or the carbamates and/or
  at least one herbicidally active compound from the group of the acetanilides with
    an isocyanate mixture which is obtained during the dimerization and/or trimerization of hexamethylene-1,6-diisocyanate, of the formula

OCH—(CH$_2$)$_6$—NCO      (I), and/or during the reaction of hexamethylene-1,6-diisocyanate, of the formula (I), with water and/or carbon dioxide,
    if appropriate in a mixture with toluylene diisocyanate
    and, if appropriate, with an organic solvent and, if appropriate, an emulsifier, β) then, in a second step, dispersing the resulting mixture in water, if appropriate as a mixture with additives, and, γ) in a third step, adding at least one diamine, polyamine, dialcohol, polyalcohol and/or aminoalcohol, if appropriate as a mixture with water and then, if appropriate, adding further additives to the resulting dispersion.

Finally, it has been found that the microcapsule formulations according to the invention are highly suitable for applying the agrochemically active compounds which they comprise to plants and/or their environment.

It is considered as extremely surprising that the microcapsule formulations according to the invention are better suited to applying the agrochemically active compounds which they contain than the constitutionally most similar prior-art preparations.

What is particularly unexpected is that, amongst the large number of candidate isocyanates, it is especially the above-mentioned isocyanate mixture, or mixture of isocyanate reaction products, which is particularly suitable for preparing microcapsule formulations which have the desired properties.

The microcapsule formulations according to the invention are distinguished by a series of advantages. Thus, they are capable of liberating the active components over a prolonged period in the particular amount required. Another advantage is that the plant tolerance of the active compounds which they contain is improved and, moreover, that the acute toxicity of the active components is also reduced, so that applying the microcapsule formulations is unproblematic for the operator, even without major safety precautions.

The microcapsule formulations according to the invention are characterized by the components contained in the dispersed phase and in the liquid phase.

The isocyanate mixture mentioned under (a) is obtained during the dimerization and/or trimerization of hexamethylene-1,6-diisocyanate and/or during the reaction of 1 mol of hexamethylene-1,6-diisocyanate and/or its dimers or trimers with 0.25 to 0.5 mol of water and/or 0.5 mol of carbon dioxide. Accordingly, these reaction products are uretidones, isocyanurates, biurets and/or oxadiazinetriones of hexamethylene-1,6-diisocyanate, of the formula (I).

Preferred mixtures are those which comprise isocyanates of the formulae

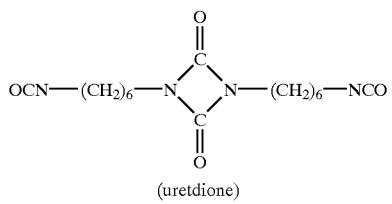
(uretdione)

-continued

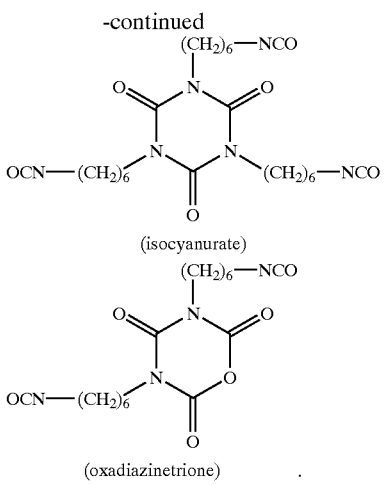

(isocyanurate)

(oxadiazinetrione)

Examples of such isocyanate mixtures which may be mentioned are:
Desmodur® N 3200
Desmodur® N 3300
Desmodur® N 3400
2H-1,3,5-oxadiazine-2,4,6-(3H,5H)-trione-3,5-bis-(6-isocyanato-hex-1-yl)

The isocyanate mixtures or reaction products of isocyanate mixtures mentioned under (a) have been disclosed (cf. WO 98-29 360). The same applies to toluylene diisocyanate, which is also mentioned under (a).

Suitable amines of the groups mentioned under (a) are, preferably, aliphatic and alicyclic primary and secondary diamines and polyamines. Examples which may be mentioned are 1,2-ethylenediamine, diethylenetriamine, triethylenetraamine, bis-(3-aminopropyl)-amine, bis-(2-methylaminoethyl)-methylamine, 1,4-diamino-cyclohexane, 3-amino-1-methyl-aminopropane, N-methyl-bis-(3-aminopropyl)-amine, 1,4-diamino-n-butane and 1,6-diamino-n-hexane.

These diamines and polyamines are known compounds of organic chemistry.

Suitable alcohols of the groups mentioned under (a) are, preferably, primary and secondary aliphatic dialcohols and polyalcohols. Examples which may be mentioned are: ethanediol, propane-1,2-diol, propane-1,3-diol, butane-1,4-diol, pentane-1,5-diol, hexane-1,6-diol, glycerol and diethylene glycol.

These dialcohols and polyalcohols are also known.

An example which may be given of one of the aminoalcohols mentioned under (a) is triethanolamine. These aminoalcohols are also known.

The microcapsule formulations according to the invention may contain one or more of the agrochemically active compounds mentioned under (b).

Preferred fungicidally active compounds in this context are amino derivatives such as 8-(1,1-dimethylethyl)-N-ethyl-N-propyl-1,4-dioxaspiro[4,5]decane-2-methanamine (spiroxamine) and fenpropidin, and also morpholine derivatives such as aldimorph, dodemorph and fenpropimorph.

Other preferred fungicidally active compounds in the present context are triadimefon, triadimenol, bitertanol, dichlobutrazole, tebuconazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, flusilazole, prochloraz, metconazole, ipconazole, fluquinconazole, triticonazole, triflumizole, imibenconazole, imazalil and 2-[2-(1-chloro-cyclopropyl)-3-(2-chlorophenyl)-2-hydroxypropyl]-2,4-dihydro-[1,2,4]-triazole-3-thione.

Insecticidally active compounds of the groups mentioned under (b) which may preferably be mentioned are azinphos-methyl, azinphos-ethyl, bromophos A, chlorpyriphos, chlorpyriphos M, dichlorphos, edifenphos, fenamiphos, isofenphos, malathion, mesulfenphos, parathion A, parathion M, pirimiphos, profenofos, pyraclophos, tebupirimfos, betacyfluthrin, cyfluthrin, cypermethrin, transfluthrin und lambda-cyhalothrin, and furthermore aldicarb, aldoxycarb, aminocarb, bendiocarb, bufencarb, butacarb, butocarboxim, butoxycarboxim, 2-sec-butyl-phenyl methylcarbamate, carbanolate, carbaryl, carbofuran, cartap, decarbofuran, dimetilan, dioxacarb, ethiofencarb, fenethacarb, formetanate, formparanate, isoprocarb, methiocarb, methomyl, mexacarbate, nabam, nitrilacarb, oxamil, pirimicarb, promecarb, propoxur, thiofanox, thiocarboxim, thiram, trimethylphenyl methylcarbamate, 3,4-xylyl methylcarbamate and 3,5-xylyl methylcarbamate.

Herbicidally active compounds of the acetanilides mentioned under (b) which may preferably be mentioned are: alachlor, acetochlor, butachlor, metazachlor, metolachlor, pretilachlor and propachlor.

Suitable additives which the microcapsule formulations according to the invention may contain are organic solvents, emulsifiers, protective colloids, thickeners, preservatives, antifoams, antifreeze agents and neutralizers.

Suitable organic solvents are all customary organic solvents which, on the one hand, are sparingly miscible with water but, on the other hand, thoroughly dissolve the agrochemically active compounds employed. The following may be mentioned as being preferred: aliphatic and aromatic, optionally halogenated hydrocarbons such as toluene, xylene, Solvesso®, tetrachloromethane, chloroform, methylene chloride and dichloroethane, furthermore esters such as ethyl acetate, and alkane carboxamides such as N,N-dimethyloctanecarboxamide and N,N-dimethyldecanecarboxamide.

Suitable emulsifiers are customary surfactants which are present in formulations of agrochemically active compounds. Examples which may be mentioned are ethoxylated nonylphenols, polyethylene glycol ethers of linear alcohols, reaction products of alkylphenols with ethylene oxide and/or propylene oxide, moreover fatty acid esters, alkylsulphonates, alkyl sulphates, aryl sulphates.

Suitable protective colloids (dispersants) are all substances which are usually employed for this purpose. The following may be mentioned as being preferred: natural and synthetic water-soluble polymers such as gelatin, starch and cellulose derivatives, in particular cellulose esters and cellulose ethers such as methylcellulose, furthermore polyvinyl alcohols, partially hydrolysed polyvinyl acetates, lignosulphonates, polyvinylpyrrolidones and polyacrylamides.

Thickeners which are suitable are all substances which can conventionally be employed for this purpose in plant treatment products. Preferred are Kelzan® (xanthan-based thixotropic thickener), silicas and attapulgite.

Suitable preservatives are all substances which are usually present in plant treatment products for this purpose. Examples which may be mentioned are Preventol® and Proxel®.

Suitable antifoams are all substances which can conventionally be employed in plant treatment products for this purpose. Silane derivatives, such as polydimethylsiloxanes, and magnesium stearate may preferably be mentioned.

Suitable substances which may act an antifreeze agents are all substances which can conventionally be used in plant treatment productions for this purpose. Examples which may be mentioned are urea, glycerol and propylene glycol.

Suitable neutralizing agents are customary acids and bases. Phosphoric acid and aqueous ammonia solution may mentioned by way of example.

The particles of the disperse phase have a mean particle size which is generally between 1 and 20 μm, preferably between 3 and 15 μm.

The aqueous phase of the microcapsule formulations according to the invention is essentially composed of water. In addition, it may also comprise additives such as emulsifiers, protective colloids, preservatives, antifoams, antifreeze agents and neutralizing agents.

Preferred components are those which have already been mentioned as being preferred for these substances. In addition, the aqueous phase may also comprise small amounts of organic solvents and of the remaining constituents of the disperse phase.

The composition of the microcapsule formulations according to the invention can be varied within a certain range. Based on the entire formulation, the disperse phase generally amounts to between 30 and 70% by weight, preferably between 40 and 60% by weight. Within the disperse phase, too, the individual components may be varied within a certain range. Thus, the concentrations in the disperse phase are as follows:

reaction product of isocyanate mixture and diamine, polyamine, dialcohol, polyalcohol and/or aminoalcohol; generally between 1 and 2% by weight, preferably between 2 and 10% by weight.

agrochemically active substances: generally between 10 and 90% by weight, preferably between 20 and 80% by weight, and additives: generally between 0 and 90% by weight, preferably between 10 and 80% by weight.

The microcapsule formulations according to the invention are prepared following the procedure for microencapsulation.

In general, a procedure is followed in which, as a first step of the process (stage α), a solution of one or more agrochemically active compounds, isocyanate mixture, and, if appropriate, organic solvent and emulsifier is preferred. If the agrochemically active compound is a solid, it is generally employed in the form of a solution in an organic solvent. If the agrochemically active compound is liquid at room temperature, an organic solvent can be dispersed with. Preferred agrochemically active compounds, organic solvents and emulsifiers are those which have already been mentioned in connection with the description of the microcapsule formulations according to the invention as being preferred.

The quantities of the individual components are chosen in such a way that they are present, in the resulting disperse phase, in those concentrations which have already been mentioned as being preferred. The ratio of the isocyanate mixture mentioned under (a) to toluylene diisocyanate may be varied within a certain ratio. In general, between 0 and 10 parts by weight, preferably between 0 and 5 parts by weight, of toluylene diisocyanate are employed per part by weight of the isocyanate mixture mentioned under (a).

The solution prepared in stage α of the process according to the invention is dispersed in the second step of the process (stage β) in water, if appropriate as a mixture with additives. Suitable additives are protective colloids and emulsifiers. Preferably suitable are those substances which have already been mentioned in connection with the description of the microcapsule formulations according to the invention as being preferred protective colloids or emulsifiers.

To prepare the dispersions, all devices which are suitable for such purposes and which produce potent shearing forces may be employed. Examples which may be mentioned are rotor/stator mixers and jet dispersing machines.

The dispersion prepared in stage β of the process according to the invention is treated in the third step of the process (stage γ) while stirring first with at least one diamine, polyamine, dialcohol, polyalcohol and/or aminoalcohol. Here, the amine or alcohol components are expediently added in the form of an aqueous solutions. After the reaction which leads to capsule formation, additives may be added, if appropriate.

Suitable reactants are preferably all those diamines, polyamines, dialcohols, polyalcohols and aminoalcohols which have already been mentioned as being preferred in connection with the description of the microcapsule formulations according to the invention.

Suitable additives for carrying out stage γ of the process according to the invention are thickeners, preservatives, antifoams, antifreeze agents and neutralizing agents. Those substances which have already been mentioned in connection with the description of the microcapsule formulations according to the invention as being preferred thickeners, preservatives, antifoams, antifreeze agents and neutralizing agents can preferably be used.

When carrying out the process according to the invention, the ratio of isocyanate to amine, or alcohol, components can be varied within a certain range. In general, 0.8 to 1.5 equivalents of amine, or alcohol, component are employed per mole of isocyanate. The quantities of isocyanate and amine, or alcohol, are preferably chosen in such a way that equimolar amounts of isocyanate groups and amino, or hydroxyl, groups are present.

When carrying out the process according to the invention, the reaction temperatures can be varied with a certain range. The process is generally carried out, when carrying out the first step, at temperatures between 0° C. and 40° C., preferably between 2° C. and 30° C., when carrying out the second step, at temperatures between −10° C. and +40° C., preferably between 0° C. and 80° C. and when carrying out the third step, at temperatures between 0° C. and 80° C., preferably between 10° C. and 75° C.

The process according to the invention is generally carried out under atmospheric pressure.

The microcapsule formulations according to the invention are outstandingly suited for applying the agrochemically active compounds which they contain to plants and/or their environment. They ensure liberation of the active components in the specific quantity desired over a prolonged period.

The microcapsule formulations according to invention can be employed in practice either as such or after previous dilution with water. They are applied by the customary methods, for example by pouring, spraying or atomizing.

The apparatus rate of the microcapsule formulations according to the invention can be varied within a substantial range. It depends on the agrochemically active compounds in question and on their content in the microcapsule formulations.

The invention is illustrated by the examples which follow.

PREPARATION EXAMPLE

Example 1

A solution of 30.36 g of β-cyfluthrin, 91.22 g of Solvesso® 150, 0.12 g of tristyrylphenol ethoxylate and 1.58 g of Desmodur® N 3200 is dispersed at 10 000 rpm in the course of one minute in 145.12 g of a 1% by weight solution of polyvinyl alcohol (Mowiol 26-88®) in water in a mixture with 0.06 g of a silicone antifoam, using a dispersing machine. 0.86 g of triethanolamine are then added. The resulting reaction mixture is heated to 70° C. in the course of one hour and held for a further 4 hours at 70° C., with gentle stirring. After the mixture has subsequently cooled to room temperature, 30.0 g of a 2% by weight solution of Kelzan S® (xanthan-based thickener) in water and 0.54 g of preservative (Preventol® D7) are added. This gives 300 g of a microcapsule formulation with a β-cyfluthrin content of 100 g/l and a mean particle size of 4.3 μm.

Example 2

A solution of 30.36 g of β-cyfluthrin, 91.22 g of Solvesso® 150, 0.12 g of tristyrylphenol ethoxylate and 3.17 g of Desmodur® N 3200 is dispersed at 17° C. at 10 000 rpm in the course of one minute in 145.12 g of a 1% by weight solution of polyvinyl alcohol (Moviol 26-88®) in water in a mixture with 0.06 g of a silicone antifoam, using a dispersing machine. 0.62 g of monoethylene glycol are then added. The resulting reaction mixture is heated to 70° C. in the course of one hour and held for a further 4 hours at 70° C., with gentle stirring. After the mixture has subsequently cooled to room temperature, 30.0 g of a 2% by weight solution of Kelzan S® (xanthan-based thickener) in water and 0.54 g of preservative (Preventol® D7) are added. This gives 300 g of a microcapsule formulation with a β-cyfluthrin content of 100 g/l and a mean particle size of 4.3 μm.

Example 3

A solution of 75.8 g of fenamiphos, 44.1 g of Solvesso® 200, 2.30 g of toluylene diisocyanate and 2.65 g of Desmodur® N 3400 is dispersed at 19° C. at 5500 revolutions per minute in the course of one minute in 141.7 g of a 1% by weight solution of polyvinyl alcohol (Mowiol 26-88®) in water in a mixture with 0.06 g of a silicone antifoam, using a dispersing machine. Then, 2.72 g of a 50% by weight solution of diethylenetriamine in water are added. The resulting reaction mixture is heated to 70° C. in the course of one hour and held for a further 4 hours at 70° C., with gentle stirring. After the mixture has subsequently cooled to room temperature, 30.0 g of a 2% by weight solution of Kelzan S® (xanthan-based thickener) in water and 0.6 g of preservative (Preventol® D7) are added. This gives 300 g of a microcapsule formulation with a fenamiphos content of 240 g/l and a mean particle size of 3.5 μm.

Example 4

A microcapsule formulation using the following substances is prepared following the method described in Example 3.

| Solution: | 75.8 g | of fenamiphos |
| | 45.4 g | of Solvesso ® 200 |
| | 2.77 g | of toluylene diisocyanate |
| | 2.16 g | of 2H-1,3,5-oxadiazine-2,4,6-(3H,5H)-trione-3,5-bis-(6-isocyanato-hex-1-yl) |
| Aqueous phase: | 140.3 g | of a 1% by weight polyvinyl alcohol solution in water |
| | 0.06 g | of silicone antifoam |
| Amine: | 2.92 g | of a 50% by weight diethylenetriamine solution |
| Additives: | 30.0 g | of a 2% by weight Kelzan ® S solution (xanthan-based thickener) |
| | 0.54 g | of preservative ((Preventol ®) D7) |

This gives 300 g of a microcapsule formulation with a fenamiphos content of 240 g/l and a mean particle size of 5.3 μm.

Example 5

A mixture of 158.9 g of tebupirimfos, 3.03 g of toluylene diisocyanate and 3.5 g of 2H-1,3,5-oxadiazine-2,4,6-(3H, 5H)-trione-3,5-bis-(6-isocyanato-hex-1-yl) is dispersed at 14° C. at 8000 rpm in the course of 30 seconds in 280.9 g of a 1% by weight solution of polyvinyl alcohol (Mowiol 26-88®) in water in a mixture with 0.1 g of a silicone antifoam, using a dispersing machine. Then, 3.6 g of a 50% by weight solution of diethylene-triamine in water are added. The resulting reaction mixture is heated to 70° C. in the course of 2 hours and held for a further 4 hours at 70° C., with gentle stirring. After the mixture has subsequently cooled to room temperature, 500 g of a 2% by weight solution of Kelzan® S (xanthan-based thickener) in water are added. This gives 500 g of a microcapsule formulation with a tebupirimfos content of 300 g/l and a mean particle size of 4.7 μm.

Example 6

A solution of 171 g of tebupirimfos, 9 g of Solvesso® 200 and 17.3 g of Desmodur® N 3300 is dispersed at 18° C. at 6000 rpm in the course of 1 minute in 251 g of a 1% by weight solution of polyvinyl alcohol (Mowiol 26-88®) in water, using a dispersing machine. Then, 26.7 g of a 10% by weight solution of ethylene-diamine in water are added. The resulting reaction mixture is heated to 55° C. in the course of 2 hours and held for a further 4 hours at 55° C., with gentle stirring. After the mixture has subsequently cooled to room temperature, 25.0 g of a 2% by weight solution of Kelzan S® (xanthan-based thickener) in water are added. This gives 500 g of a microcapsule formulation with a tebupirimfos content of 320 g/l and a mean particle size of 5.1 μm.

Use Example

To check the release of active compound, in each case 3 g of a microcapsule formulation are suspended in 1 liter of water and the suspension is stirred for 48 hours at room temperature. Then, 5-ml-samples are taken and centrifuged to separate the microcapsules. The active compound content in the remaining aqueous phase is determined by HPLC.

The results can be seen from the table which follows.

TABLE 1

| Example No. | Active compound content |
|---|---|
| 3 | 87 ppm |
| 4 | 56 ppm |

What is claimed is:
1. A microcapsule formulation comprising
  A) a particulate disperse phase of
    a) a reaction product of
      one or more compounds selected from diamines, polyamines, dialcohols, polyalcohols and aminoalcohols with an isocyanate mixture comprising one or more isocyanates selected from the compounds of the formulae

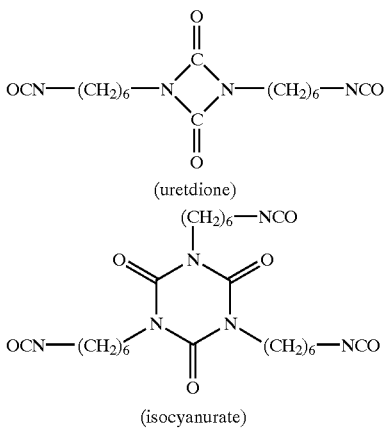

(uretdione)

(isocyanurate)

and

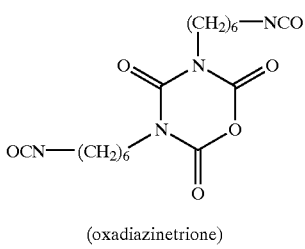

(oxadiazinetrione)

wherein said isocyanate mixture prior to its reaction is obtained during the dimerization or trimerization of hexamethylene-1,6-diisocyanate of the formula

$$OCH-(CH_2)_6-NCO \qquad (I)$$

or during the reaction of hexamethylene-1,6-diisocyanate of the formula (I) with water or carbon dioxide or with water and carbon dioxide;

b) one or more fungicidally active compounds selected from the group consisting of 8-(1,1-dimethylethyl)-N-ethyl-N-propyl-1,4-dioxaspiro[4,5]decane-2-methanamine (spiroxamine), fenpropidin, aldimorph, dodemorph, fenpropimorph triadimefon, triadimenol, bitertanol, dichlobutrazole, tebuconazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, flusilazole, prochloraz, metconazole, ipconazole, fluquinconazole, triticonazole, triflumizole, imibenconazole, imazalil and 2-[2-(1-chloro-cyclo propyl)-3-(2-chlorophenyl)-2-hydroxypropyl]-2,4-dihydro-[1,2,4]-triazole-3-thione,
and/or one or more insecticidally active compounds selected from the group of the phosphoric esters, the pyrethroids or the carbamates,
and/or one or more herbicidally active compounds selected from the group of the acetanilides, and c) optionally, one or more additives, the particles of the disperse phase having a mean particle size of between 1 and 20 μm, and B) a liquid aqueous phase, wherein said particulate phase is dispersed in said liquid aqueous phase to provide said microcapsule formulation.

2. A microcapsule formulation according to claim 1, wherein the isocyanate mixture comprises toluylene diisocyanate as an additional isocyanate.

3. A microcapsule formulation according to claim 1 comprising fenpropidin as said fungicidally active compound.

4. A microcapsule formulation according to claim 1 comprising fenamiphos as said insecticidally active compound.

5. A microcapsule formulation according to claim 1 comprising spiroxamine as said fungicidally active compound.

6. A microcapsule formulation according to claim 1 comprising tebupirimfos as said insecticidally active compound.

7. A microcapsule formulation according to claim 1 comprising cyfluthrin as said insecticidally active compound.

8. A microcapsule formulation according to claim 1 comprising beta-cyfluthrin as said insecticidally active compound.

9. A process for preparation of said microcapsule formulation according to claim 1, which process comprises the steps of:

a) mixing in a first step,
one or more fungicidally active compounds selected from the group consisting of 8-(1,1-dimethylethyl)-N-ethyl-N-propyl-1,4-dioxaspiro[4,5]decane-2-methanamine (spiroxamine), fenpropidin, aldimorph, dodemorph, fenpropimorph, triadimefon, triadimenol, bitertanol, dichlobutrazole, tebuconazole, propiconazole, difenoconazole, cyproconazole, flutriafol, hexaconazole, myclobutanil, penconazole, etaconazole, bromuconazole, epoxiconazole, fenbuconazole, tetraconazole, diniconazole, flusilazole, prochloraz, metconazole, ipconazole, fluquinconazole, triticonazole, triflumizole, imibenconazole, imazalil and 2-[2-(1-chloro-cyclo-propyl)-3-(2-chlorophenyl)-2-hydroxypropyl]-2,4-dihydro-[1,2,4]-triazole-3-thione, and/or one or more insecticidally active compounds selected from the group of the phosphoric esters, the pyrethroids or the carbamates, and/or one or more herbicidally active compounds selected from the group of the acetanilides, with an isocyanate mixture comprising one or more isocyanates selected from the compounds of the formulae

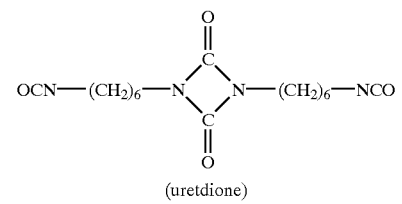

(uretdione)

-continued

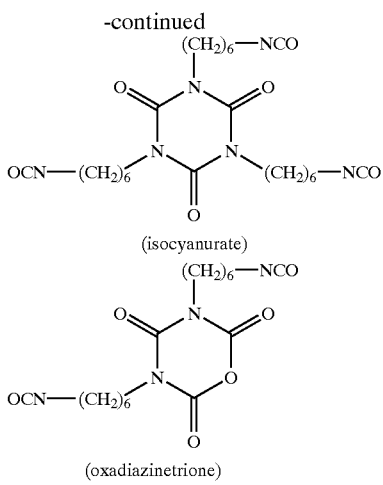

(isocyanurate)

(oxadiazinetrione)

and wherein said isocyanate mixture prior to its reaction is obtained during the dimerization or trimerization of hexamethylene-1,6-diisocyanate of the formula $$OCH\text{---}(CH_2)_6\text{---}NCO \qquad (I)$$

or during the reaction of hexamethylene-1,6-diisocyanate of the formula (I) with water or carbon dioxide or with water and carbon dioxide, β) then in a second step, dispersing the resulting mixture in water or in a mixture of water and optionally, one or more additives, and γ) in a third step, adding one or more compounds selected from diamines, polyamines, dialcohols, polyalcohols and aminoalcohols, optionally in admixture with water, and then optionally adding one or more additional additives to the resulting dispersion whereupon a particulate phase is dispersed in a liquid aqueous phase to provide said microcapsule formulation.

* * * * *